US011073506B2

(12) United States Patent
Paltauf et al.

(10) Patent No.: US 11,073,506 B2
(45) Date of Patent: Jul. 27, 2021

(54) METHOD FOR DETECTING THE RANCIDITY OF OILSEEDS, SEEDS AND NUTS

(71) Applicants: INSORT GMBH, Kirchberg a.d. Raab (AT); TECHNISCHE UNIVERSITAT GRAZ, Graz (AT)

(72) Inventors: Gunther Wolfgang Paltauf, Graz (AT); Erich Leitner, Graz (AT)

(73) Assignee: INSORT GMBH, Kirchberg A.D. Raab (AT)

( * ) Notice: Subject to any disclaimer, the term of this patent is extended or adjusted under 35 U.S.C. 154(b) by 107 days.

(21) Appl. No.: 16/606,907

(22) PCT Filed: Apr. 20, 2018

(86) PCT No.: PCT/AT2018/060075
§ 371 (c)(1),
(2) Date: Oct. 21, 2019

(87) PCT Pub. No.: WO2018/191768
PCT Pub. Date: Oct. 25, 2018

(65) Prior Publication Data
US 2020/0378941 A1 Dec. 3, 2020

(30) Foreign Application Priority Data

Apr. 21, 2017 (AT) .............................. A 50322/2017

(51) Int. Cl.
*G01J 3/00* (2006.01)
*G01N 33/02* (2006.01)
(Continued)

(52) U.S. Cl.
CPC ........... *G01N 33/025* (2013.01); *B07C 5/342* (2013.01); *G01N 33/03* (2013.01)

(58) Field of Classification Search
CPC .. G01N 21/314; G01N 21/33; G01N 21/3504; G01J 3/10; G01J 3/42
(Continued)

(56) References Cited

U.S. PATENT DOCUMENTS

| 2011/0267603 | A1* | 11/2011 | Shaw | ................... G01N 21/552 356/128 |
| 2013/0278919 | A1 | 10/2013 | Kawamura | |
| 2016/0313242 | A1* | 10/2016 | Margalit | ................... G01J 4/00 |

FOREIGN PATENT DOCUMENTS

EP  1332354  8/2013

OTHER PUBLICATIONS

Arantzazu Valdes et al: "Monitoring the oxidative stability and volatiles in blanched, roasted and fried almonds under normal and accelerated storage conditions by DSC, thermogravimetric analysis and ATR-FTIR : Effect of cooking on the oxidative stability of almonds", European Journal of Lipid Science and Technology., vol. 117, No. 8, Feb. 24, 2015 (Feb. 24, 2015), pp. 1199-1213.
(Continued)

*Primary Examiner* — Md M Rahman
(74) *Attorney, Agent, or Firm* — Workman Nydegger

(57) ABSTRACT

Establishing a rancidity index table and allocating a rancidity index value to an absorption or reflection spectrum of oil fruits, nuts and seeds (2) comprises:
irradiating a sample of an oil fruit, a nut or a seed (2) with a light source (3),
projecting the reflected and/or transmitted light onto a photosensor (4),
detecting the absorption or reflection spectrum by means of the photosensor (4),
extracting ingredients of the sample by determining volatile compounds,
separating volatile components of the sample by means of gas chromatography,
(Continued)

identifying separated volatile components by mass spectroscopic detection of relevant ones, determining a rancidity index value of the sample from identified volatile components of the sample, allocating the detected absorption or reflection spectrum of the sample to the rancidity index value, repeating the previous steps for a representative number of samples and forming a rancidity table from the determined rancidity index values and allocated absorption or reflection spectra.

20 Claims, 2 Drawing Sheets

(51) Int. Cl.
*B07C 5/342* (2006.01)
*G01N 33/03* (2006.01)

(58) Field of Classification Search
USPC .......................................................... 356/51
See application file for complete search history.

(56) References Cited

OTHER PUBLICATIONS

Beltran A et al: "Monitoring the oxidation of almond oils by HS-SPMEGCMS and ATR-FTIR: Application of volatile compounds determination to cultivar authenticity", Food Chemistry, Elsevier Ltd, NL, vol. 126, No. 2, Nov. 10, 2010 (Nov. 10, 2010), pp. 603-609.

Borras Eva et al: "Olive oil sensory defects classification with data fusion of instrumental techniques and multivariate analysis (PLS-DA)", Food Chemistry, Elsevier Ltd, NL, vol. 203, Feb. 4, 2016 (Feb. 4, 2016), pp. 314-322.

International Search Report issued in PCT/AT2018/060075 dated Aug. 16, 2018.

* cited by examiner

METHOD FOR DETECTING THE RANCIDITY OF OILSEEDS, SEEDS AND NUTS

The invention relates to a process for establishing a rancidity index table and allocating a rancidity index value to an absorption or reflection spectrum of oil fruits, nuts and seeds. Furthermore, it relates to a process for the detection of rancidity in an oil fruit, a nut or a seed.

Furthermore, the invention relates to a device for the detection of rancid oil fruits, nuts or seeds.

The detection and subsequent sorting of bulk materials by means of photosensors is a widely used method. One embodiment of such a process and such a device for sorting seeds is described, for example, in the publication US 2013/0278919 A1. In this known process, seeds are individually examined spectroscopically by being irradiated with a light source. Subsequently, an absorption or reflection spectrum is captured by a photosensor. Thereupon, a computer unit analyzes the absorption or reflection spectrum of each seed in a region of interest and calculates the content of a particular ingredient of the seed based on a calibration curve.

The identification of various ingredients in individual elements of a bulk material is of interest, for example, so as to be able to distinguish between spoiled elements and non-spoiled elements of the bulk material. According to the prior art, such processes usually operate in the near infrared range. So as to enable the use of those processes in production facilities, it is necessary for the employed photosensors to have high refresh rates, generally of 300 Hz or more. Thus, it becomes possible to ensure a high throughput while, at the same time, reliably analyzing the ingredients of each individual element that is examined. Conventionally, data collected by the photosensors are analyzed by means of common statistical classification methods such as partial least squares, principle component regression or the like. This qualitative analysis produces very good results if there are clear differences between spoiled elements and non-spoiled elements in the absorption or reflection spectrum.

Such processes have turned out to be disadvantageous in that, if the absorption or reflection spectra become too similar, the attempt to separate spoiled elements from non-spoiled elements usually leads to a large number of mis-classifications. A particular disadvantage is that, in case of a subsequent sorting, this leads to a lot of waste of non-spoiled elements. At the same time, the disadvantage arises that only a very low detection rate of spoiled elements is realized. Especially in natural products such as food, this adverse effect is particularly pronounced, since the natural spectral scattering of non-spoiled elements is very wide in comparison to elements that have been produced in a controlled way, such as, for example, plastic flakes.

Particularly in connection with oil fruits, nuts and seeds which are processed in production facilities in an automated fashion, there is considerable interest in automatically distinguishing rancid, and thus spoiled, elements from non-rancid elements.

The taste quality of nuts and other seeds or oil fruits is often impaired by lipid oxidation, which results in undesirable rancid flavours. The lipid oxidation of nuts and other oil fruits with a high fat content and, as a result, rancidity can occur in the course of storage and processing. This severely impairs the sensory characteristics (decreased enjoyment quality) and leads to a product of lower value.

The mechanisms of lipid oxidation are well known and described in the literature. There are two different mechanisms which cause rancidity. Hydrolytic rancidity is caused by the reaction of water with lipids in the presence of enzymatic activity (lipase). Oxidative rancidity can be divided into autooxidative, photooxidative and enzymatic oxidation reactions. The fatty acid composition is crucial, among other factors, in terms of the stability of the product. The stability of unsaturated acids decreases dramatically by increasing the degree of unsaturation. The oxidation rate of the fatty acids is about 1:10:100:200 for stearic acid (18:0), oleic acid (18:1, ω–9), linoleic acid (18:2, ω–6) and α-linolenic acid (18:3, ω–3).

Different methods can be employed for determining rancidity. Most methods require a large amount of sample so that a homogeneous mixture of ground oil fruits, nuts or, respectively, seeds is used. This involves the disadvantage that, by homogenizing a large number of oil fruits, nuts or, respectively, seeds, valuable information of individual ones is lost. Another drawback of the known methods is the fact that those methods are mere laboratory methods which are unsuitable for use in automated detection methods and sorting facilities. In addition, those laboratory methods are extremely time-consuming and, as mentioned above, applicable to homogenized products, but not to individual oil fruits, seeds and nuts.

From the document A. Beltran, M. Ramos, N. Grané, M. L. Martin, M. C. Garrigós, Monitoring the oxidation of almond oils by HS-SPME-GC-MS and ATR-FTIR: Application of volatile compounds determination to cultivar authenticity, Food Chemistry, Volume 126, Issue 2, 2011, pages 603-609, a process for the determination of volatile constituents of almond oils for verifying the cultivar authenticity of almonds is known. More specifically, this process serves for distinguishing between Spanish and American almond crops and possible counterfeits. For this purpose, the oxidative process of these oils is monitored by solid phase microextraction/gas chromatography—mass spectrometry (HS-SPME/GC-MS) and total reflection Fourier transform infrared spectroscopy (ATR-FTIR). For accelerating the lipid oxidation, a heat treatment is performed on the samples at 100° C. for 1, 3, 5, 7, 10, 15 and 20 days, and the oxidative stability of the samples is checked after those heat treatments. Changes observed in the infrared spectral bands are used for monitoring the progression of the oxidation of almond oils. The rancidity of almonds is not explicitly mentioned, but only an "off-flavour development" is brought up.

This study was not conducted on individual almond kernels, but on almond oil derived from a plurality of almonds, i.e., from a homogenized product. It is neither mentioned nor suggested how it might be possible to accomplish the detection and, optionally, segregation of individual almonds in a product stream, using the results of this study. Instead, the study was aimed at proposing a process based on HS-SPME coupled with GC-MS by means of which it should be possible to rapidly analyze and characterize volatile components in almond oils which result from the lipid oxidation. In addition to the measurement by means of HS-SPME/GC-MS, the ATR-FTIR spectra of almond oils were also monitored during the oxidation process. It is noted that, in the HS-SPME-GC-MS analysis, the optimal time for the oxidative heat treatment of the samples is seven days, since only after that time significant differences in the aldehyde content are discernible and this time constitutes a "reasonably short duration" of the analysis time. As far as the additional analysis by ATR-FIR is concerned, it is explained that the samples were measured after heat treatment times of 1 to 20 days under oxidative conditions, wherein, after heat treatment times of one, three and five days, significant differences in the obtained spectra were still not found. Only after the fifth day of heat treatment, spectral changes could be observed which pointed to a progressive oxidation of the samples. The measurements with HS-SPME/GC-MS or, respectively, with ATR-FTIR were performed independently of each other, and the measuring results from both types of measurement merely served for determining as to whether the result of the respective other type of measurement is plausible. However, the results of the two types of measurement are not linked. In particular, a rancidity index or any other index is not established from the measuring results.

In the document Borrás E, Ferré J, Boqué R, Mestres M, Acenia L, Calvo A, Busto O. Prediction of olive oil sensory descriptors using instrumental data fusion and partial least squares (PLS) regression. Talanta. 2016 Aug. 1; 155: 116-23. Epub 2016 Apr. 20, the use of mass spectrometry (HS-MS), Fourier transform mid-infrared spectroscopy (FT-MIR) and UV-visible light spectrophotometry (UV-vis) for predicting olive oil taste parameters is described. Using partial least squares regression, multivariate calibration models were established based on the measured values of 343 olive oil samples from four consecutive harvests. HS-MS and FT-MIR results were either evaluated individually or—to improve the predictive model—linked by "data fusion", which is the pooling of two result matrices of the two different types of measurement to form one matrix. However, in the course of this examination it became apparent that the "data fusion" was also unable to provide a useful prediction of rancidity in olive oil, since only 10% (!) of the samples with rancid olive oil could be detected correctly. As a consequence of this poor result, the authors of D2 stated that it was not possible to establish usable rancidity models from the measurement data.

The invention is thus based on the object of providing a process which avoids the disadvantages of the prior art as described and enables an automated detection of rancidity in individual oil fruits, nuts and seeds.

According to the invention, this object is achieved by a process for establishing a rancidity index table and allocating a rancidity index value to an absorption or reflection spectrum of oil fruits, nuts and seeds, comprising the steps of:

irradiating a sample of an oil fruit, a nut or a seed with a light source, projecting the reflected and/or transmitted light onto a photosensor, detecting the absorption or reflection spectrum of the sample in a wavelength range from 900 to 2500 nm, preferably from 900 to 1700 nm, more preferably from 1000 to 1500 nm, by means of the photosensor, extracting ingredients of the sample by sample preparation techniques based on a determination of volatile compounds from a vapour space above the sample, preferably by solid phase microextraction, separating volatile components of the sample by applying gas-chromatographic techniques, identifying separated volatile components of the sample by mass spectroscopic detection of constituents of the volatile components which are relevant for lipid oxidation, determining a rancidity index value of the sample from identified volatile components of the sample, allocating at least individual characteristic wavelengths or wavelength ranges of the detected absorption or reflection spectrum of the sample to the rancidity index value, repeating the previous steps for a representative number of samples and forming a rancidity table from the determined rancidity index values and allocated absorption or reflection spectra or, respectively, characteristic wavelengths or wavelength ranges of the detected absorption or reflection spectra.

In contrast to analytical, enormously time-consuming methods in the laboratory, such as the above-described known processes, this process according to the invention is suitable for use for the automated detection and sorting of oil fruits, seeds and nuts, depending on their level of rancidity, wherein a high product throughput of individual fruits is detectable and detected rancid fruits are separable individually from the product stream in sorting facilities.

In a preferred embodiment of the invention, identifying the volatile components of the sample by mass spectroscopic detection of constituents relevant for lipid oxidation comprises identifying one or more groups of substances/functional groups selected from:

hydroperoxides
    cyclic hydroperoxides
    saturated, mono- and di-unsaturated aldehydes
    hydrocarbons (alkanes, alkenes)
    alcohols (saturated and unsaturated)
    ketones (saturated and unsaturated)
    short chain fatty acids
    alkyl furans.

The identification of the volatile components of the sample by mass spectroscopic detection of constituents relevant for lipid oxidation may occur, in particular, by establishing chromatograms at mass/charge ratios selected in a range of between 20 and 300, preferably at at least one mass/charge ratio selected from 43, 44, 55, 56, 57, 60, 70, 71, 73, 74, 81, 83, 97.

In a specific embodiment of the invention, the identification of the volatile components of the sample by mass spectroscopic detection of constituents relevant for lipid oxidation comprises establishing a fatty acid chromatogram at a first mass/charge ratio and an aldehyde chromatogram at a second mass/charge ratio.

The samples with which the process according to the invention is carried out are selected in terms of number and characteristic in such a way that a representative cross-section of possible rancidities can be determined. This can be ensured, inter alia, by adequate sample selection and preparation (e.g., storage at an elevated temperature for different time periods).

For measuring the absorption or reflection spectra of oil fruits, nuts or, respectively, seeds by hyperspectral imaging (HSI) for the determination of rancidity and the subsequent sorting as preferred by the invention, detailed information on individual oil fruits, nuts or, respectively, seeds is essential for a proper calibration model. This is ensured by the process according to the invention, whereby a segregation of rancid oil fruits, nuts or, respectively, seeds can be achieved which is far more unerring than before. In particular, the invention provides a highly accurate and distinctive reference analysis by means of which the actual oxidation status of individual nuts/oil fruits/seeds can be determined, and extreme values thereof can be gathered.

One embodiment of the process according to the invention is based on the accumulation of volatile compounds in the vapour space above the sample, specifically on headspace solid phase microextraction (HS-SPME), coupled to a gas chromatograph with mass-selective detection. This combination of analytical methods is abbreviated as HS-SPME-GC-MS. However, the invention is not limited to this embodiment, but the process according to the invention basically comprises the measurement and determination of volatile compounds in the vapour space of the sample, separating individual constituents of the volatile compounds by gas chromatography, identifying at least individual ones of the separated volatile compounds by mass-selective detection and selectively using identified volatile compounds for determining the rancidity index.

The lipid oxidation of unsaturated fatty acids begins with the formation of hydroperoxides and results in a large group of different chemical structures and functional groups. Thus, those groups of substances can potentially be used as marker compounds for measuring the degree of lipid oxidation.

It is recommended to consider, for the hyperspectral analysis, all wavelengths in the near infrared range which are able to measure the structural properties as described above.

Compounds which are responsible for an undesirable rancid taste are, for example, aldehydes which are derived from the fatty acid chain cleavage after the hydroperoxide formation. With ongoing oxidation, the aldehydes can form free fatty acids, which may also contribute to further undesirable sensory characteristics of rancid nuts. For the evaluation of the quality of individual oil fruits or seeds, these (with different rancidities and different origins) are first measured by HSI, marked individually in a timely manner and packaged and analyzed by HS-SPME-GC-MS as follows:

Individual oil fruits, nuts or seeds are ground and a suitable representative amount of sample, e.g. 300 mg, is weighed into a glass vessel of a suitable size and is sealed in a gas-tight manner. A glass-coated magnetic stirrer may be contained in the glass vessel. An accumulation of volatile components is accomplished by suitable techniques based on a headspace analysis of suitable ad- or absorptive materials capable of reversibly binding volatile organic compounds. Furthermore, desorption takes place thermally at elevated temperatures, preferably directly in the inlet system of a gas chromatographic system. The separation of the volatile compounds occurs on high-resolution capillary columns with a suitable stationary phase and a temperature program capable of separating the analytes. The detection occurs via a mass-selective detection in such a way that a mass spectrum can be captured across the entire mass range of the relevant target compounds in order to enable unambiguous identification of the compounds. Mass spectra are detected in a scan mode with a scan range of mass/charge ratios (m/z) of preferably 20-300.

Further information can be obtained by extracting chosen mass/charge ratios. It has been shown that m/z=44 constitutes a universal and chosen fragment for linear and saturated aldehydes, which is perfectly suitable for the determination of rancidity. Additional information on potential rancidity can be obtained via a free fatty acid using the mass/charge ratio m/z=60. According to one embodiment of the process, the aldehyde chromatogram is consequently established at an m/z of 44, and the fatty acid chromatogram is established at an m/z of 60.

In one embodiment of the invention, a rancidity index value can be calculated by integrating the peaks of the aldehyde chromatogram with an m/z of 44 and those of the fatty acid chromatogram with an m/z of 60. The numbers which are obtained can be expressed either as an aldehyde index value or as a fatty acid index value or as a total rancidity index. For ease of readability, the sum of the peak ranges is divided by a fixed number in order to obtain a number which is more convenient to handle. By analyzing a large group of different samples of various origins and qualities, a wide range of rancidity index values can be determined and, respectively, verified, which are used for the calibration model.

The process according to the invention thus uses a quantitative approach which does not involve searching for obvious distinguishing features in the absorption or reflection spectra, but establishes a correlation between slight, but still significant differences in the absorption or reflection spectra and a reference from the laboratory. The absorption or reflection spectra are thus not used for dividing oil fruits and seeds into two categories of "good" (hardly any to no products of a rancidity reaction) and "bad" (products of a rancidity reaction are present), but a rancidity index is established. As a result, the advantage is obtained that the degree of rancidity can thus be detected quantitatively. It is particularly advantageous that, only in a subsequent step, one or more threshold values for the rancidity index can be provided from which an oil fruit, a nut or, respectively, a seed is classified as no longer conforming to quality standards or, respectively, as falling under different quality levels. In particular, this allows the advantage of a very simple adaptation to different quality requirements for oil fruits and seeds.

The process according to the invention furthermore provides the advantage that identifiability of rancidity in oil fruits and seeds by means of spectrometry is rendered possible for the first time. For this purpose, chemical markers were found in the laboratory which correlate directly with rancidity. Thereupon, using statistical correlation methods, the absorption or reflection spectra of the photosensor, which had been recorded for selected samples, were again correlated to the rancidity index determined for the same samples in the laboratory so that the rancidity index can be calculated directly from the absorption or reflection spectrum.

Advantageous embodiments of the process according to the invention as well as alternative embodiment variants are explained in further detail below with reference to the figures.

The process according to the invention provides an allocation of a rancidity index value to individual oil fruits, nuts and seeds 2, wherein, in a first process stage, an individual oil fruit, nut or seed 2 is irradiated with a light source 3. According to a preferred embodiment variant, this occurs in the near infrared range. The light reflected from or, respectively, transmitted through the oil fruit, nut or seed 2 is subsequently projected onto a photosensor 4 which detects an absorption or reflection spectrum in a near infrared range of from 900 to 2500 nm, preferably from 900 to 1700 nm. In a particularly preferred embodiment variant, the absorption or reflection spectrum is detected by the photosensor 4 in a range of from 1000 to 1500 nm. In a preferred embodiment variant, the absorption or reflection spectrum is detected by hyperspectral detection.

In order to determine the rancidity index value of the oil fruit, nut or seed 2 the absorption or reflection spectrum of which has previously been detected, the volatile fraction shall be enriched with suitable ad- and/or absorptive materials by headspace analysis of the volatile fraction of individual homogenized oil fruits/seeds/nuts, immediately after the measurement of the spectrum. Upon thermal desorption, separation and detection occur on a gas chromatographic system with mass-selective detection. The selection of appropriate selective mass fragments of the breakdown products formed by lipid oxidation allows an unambiguous allocation to relevant substance classes, hence for establishing a suitable calibration model for the spectral data from the spectrum measurement, in particular the HSI measurement.

In a preferred embodiment variant, the determination of an aldehyde index value is effected by integration across at least a portion of a determined aldehyde chromatogram, and the determination of a fatty acid index value is effected by integration across at least a portion of a determined fatty acid chromatogram.

Figure 1:
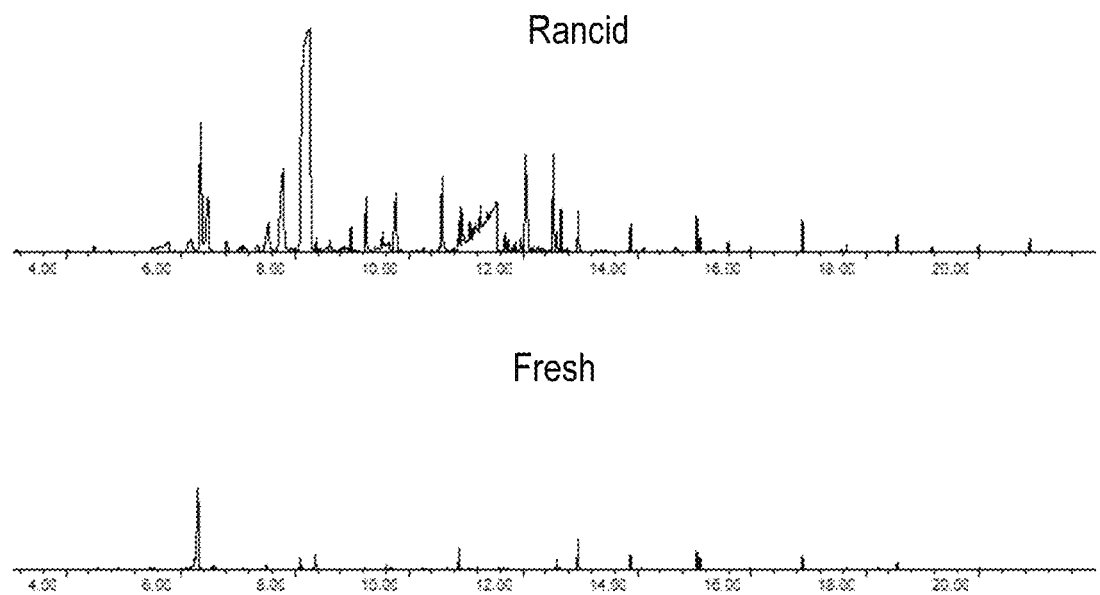
FIG. 1 shows a chromatogram of a rancid sample and a fresh sample.

For illustrative purposes, FIG. 1 shows a chromatogram of a rancid sample and a fresh sample which have been analyzed according to the previously described process, the mass spectrometer being operated for the detection in a scan mode of mass/charge ratios (m/z) in a relevant mass range of, e.g., 20-300.

Figure 2:
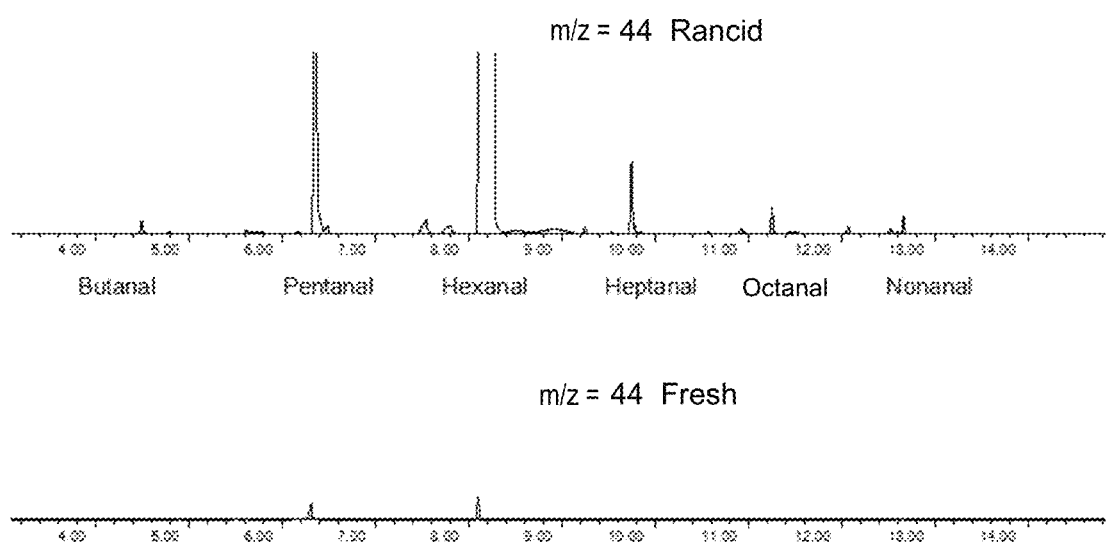
FIG. 2 shows a chromatogram of the extracted m/z 44 (saturated aldehydes) of a rancid and a fresh nut.

For illustrative purposes, FIG. 2 shows an example of an aldehyde chromatogram of a rancid sample at the first mass/charge ratio (m/z) of 44, in comparison to a fresh sample. The determination of the aldehyde index value as described above obviously results in an aldehyde index value which is considerably higher for the aldehyde chromatogram of the rancid sample than for the good sample.

Figure 3:
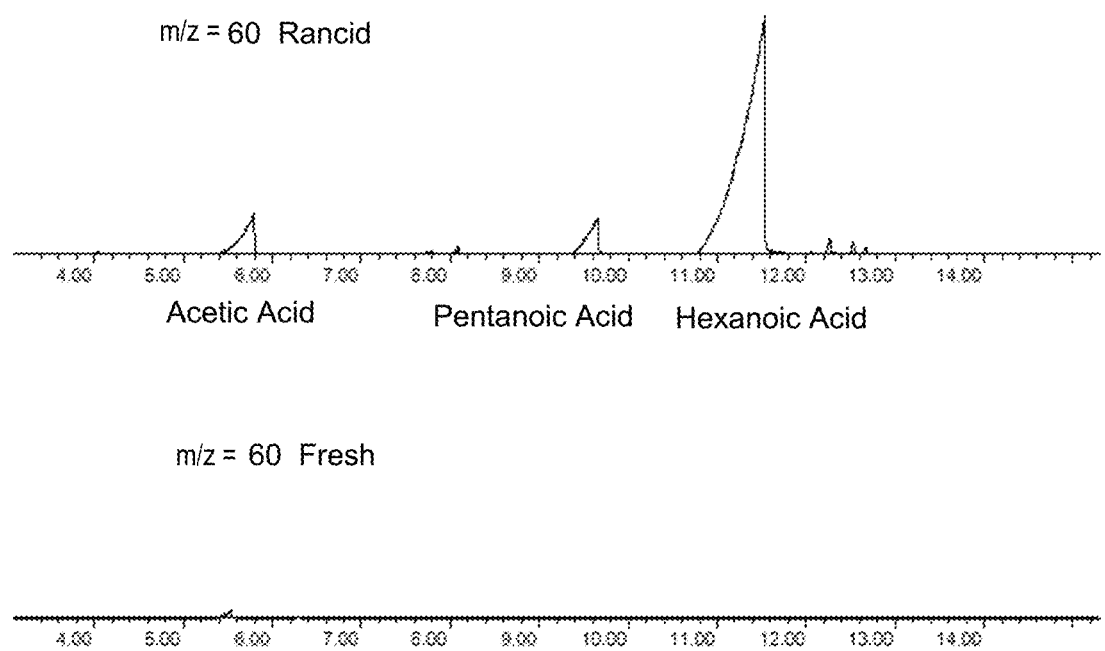
FIG. 3 shows chromatograms of the extracted m/z 60 (fatty acids) of a rancid and a fresh nut.

For illustrative purposes, FIG. 3 shows an example of a fatty acid chromatogram of a rancid sample at the second mass/charge ratio (m/z) of 60, in comparison to a fresh sample. The determination of the fatty acid index value as described above obviously leads to a fatty acid index value which is considerably higher for the fatty acid chromatogram of the rancid sample than for the fresh sample, in line with the aldehyde index value described in FIG. 2.

Those steps are repeated for a representative variety of oil fruits, nuts or, respectively, seeds, and a rancidity index table is created from the determined rancidity index values and the allocated absorption and reflection spectra.

In a preferred embodiment variant of the process, the allocation of the detected absorption or reflection spectrum of the oil fruit, nut or seed to the rancidity index value is effected by allocating the rancidity index value to at least one of an average, a bandwidth or individual frequency bands of the detected absorption or reflection spectrum. In doing so, certain ranges or an average of the respective absorption or reflection spectrum is/are defined as ranges which are characteristic of the degree of rancidity of the oil fruits, nuts or seeds 2.

Furthermore, the invention provides a process for the detection of the rancidity of an oil fruit, a nut or a seed 2 in order to solve the problems as initially indicated. In this detection process, an individual oil fruit, nut or seed is irradiated with a light source in a first process stage. According to a preferred embodiment variant, this is likewise effected in the near infrared range.

The light reflected from or, respectively, transmitted through the oil fruit, nut or seed is subsequently projected onto a photosensor which detects an absorption or reflection spectrum in a near infrared range of preferably from 900 to 1700 nm. In a particularly preferred embodiment variant, the absorption or reflection spectrum is detected by the photosensor in a range of from 1000 to 1500 nm. Preferably, the detection of the absorption or reflection spectrum is effected by hyperspectral detection by means of a hyperspectral camera.

In a further step, this process makes use of the rancidity table of the previously described process, which contains the rancidity index values and the allocated absorption or reflection spectra or, respectively, characteristic ranges and/or wavelengths of those spectra. This is followed by a comparison of the absorption or reflection spectrum detected in said process with the absorption or reflection spectra contained in the rancidity index table. In this way, an allocation of the detected absorption or reflection spectrum to an absorption or reflection spectrum of the rancidity index table which is most similar to the detected absorption or reflection spectrum is accomplished. This allows the determination of the rancidity index value allocated to the most similar absorption or reflection spectrum.

This process provides the advantage that the detection of the rancidity of an oil fruit, a nut or a seed is rendered possible in a production facility by a previous calibration by means of the previously described process according to the invention for establishing a rancidity index table, wherein the rancidity of individual fruits is detected, rather than only a homogeneous product stream.

According to a preferred embodiment variant of the detection process according to the invention, the allocation of the detected absorption or reflection spectrum to an absorption or reflection spectrum of the rancidity index table which is most similar to the detected absorption or reflection spectrum is effected by comparing at least one of an average, a bandwidth or individual frequency bands of the absorption or reflection spectra. In doing so, certain ranges or an average of the respective absorption or reflection spectrum is/are defined as ranges which are characteristic of the degree of rancidity of the oil fruits, nuts or seeds and is/are used for this comparison. This advantageously increases the accuracy of the process.

Furthermore, this detection process provides the advantage that, in a further process stage, at least one threshold value can be determined, and exceeding this at least one threshold value causes the oil fruit, nut or seed to be discarded or to be sorted in a differentiated manner. This provides the advantage that the definition of a threshold value makes it possible to adapt to different quality requirements for the oil fruits, nuts or, respectively, seeds.

Figure 4:
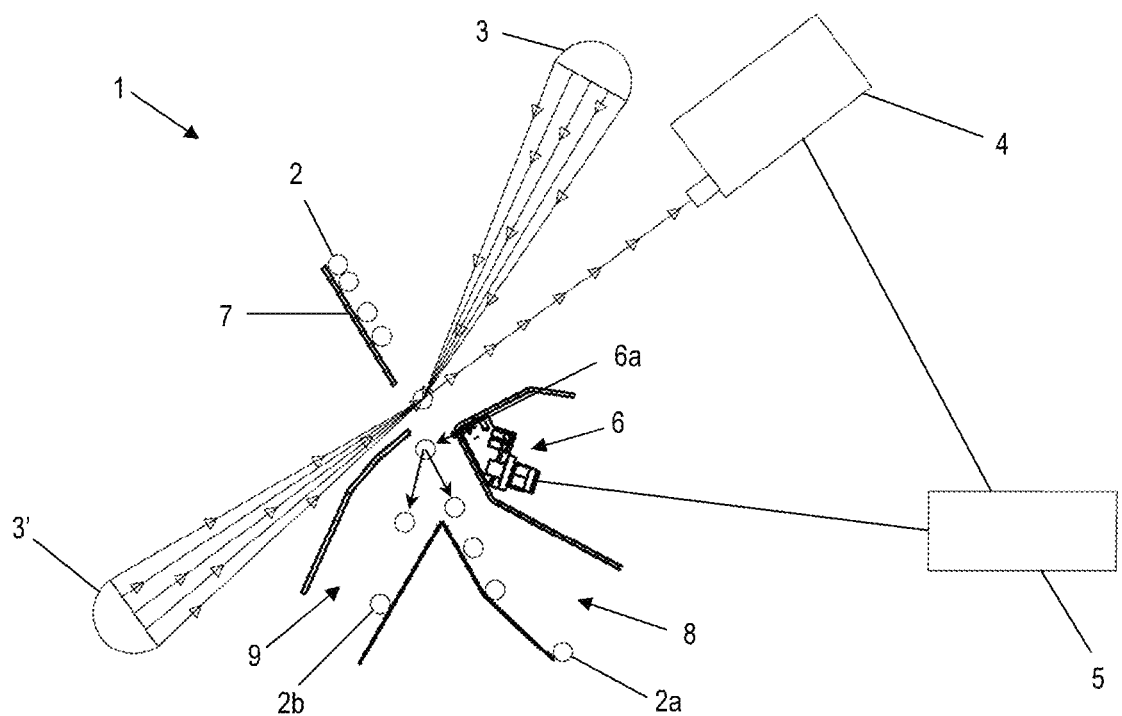
FIG. 4 shows a device for detecting rancid oil fruits, nuts or seeds in a schematic illustration.

Finally, the invention also comprises a device for the detection of rancid oil fruits, nuts or seeds, which will be described in detail below, this device being designed for executing the detection process according to the invention, using a rancidity index table established according to the process of the invention for establishing a rancidity index table. FIG. 4 shows a device 1 according to the invention for the detection of rancid oil fruits, nuts or seeds 2 in a schematic illustration, which comprises two light sources 3, 3', which may be provided together or alternatively, a photosensor 4, a computer unit 5 and a sorting unit 6. Using a transport device 7 in the form of a chute, the oil fruits, nuts or seeds 2 are consecutively guided past and through the light beams emitted by the light source 3, 3a and irradiated by them. According to a preferred embodiment variant, the light sources 3, 3' emit light in the near infrared range. The photosensor 4 detects the light of the light source 3 reflected from the oil fruit, the nut or, respectively, the seed 2 or the transmitted light of the light source 3' and detects the absorption or reflection spectrum of the oil fruit, nut or seed 2.

The photosensor 4 is connected to the computer unit 5 and transmits the detected absorption or reflection spectrum to it.

The computer unit 5 makes use of the rancidity index table for evaluating the absorption or reflection spectrum according to the process first described herein. Said table contains a number of rancidity index values and allocated absorption or reflection spectra. The computer unit 5 compares the detected absorption or reflection spectrum to the absorption or reflection spectra listed in the rancidity index table and allocates the detected absorption or reflection spectrum to the most similar absorption or reflection spectrum of the rancidity index table. This is done according to a preferred embodiment variant by comparing an average, a bandwidth or individual frequency bands of the absorption or reflection spectra, or a combination thereof. After the allocation has been made, the computer unit determines the rancidity index value allocated to the most similar absorption or reflection spectrum. In this way, a rancidity index value is allocated to each individual oil fruit, nut or, respectively, seed 2 detected by the device 1.

Downstream of the photosensor 4, the oil fruits, nuts or seeds 1 are guided past the sorting unit 6, which is likewise connected to the computer unit 5, with the computer unit 5 controlling the sorting unit 6. The sorting unit 6 allows sorting of individual oil fruits, nuts or seeds 2 from a product stream of oil fruits, nuts or seeds 2 guided through the device 1, e.g., by means of bursts of compressed air 6a, which convey the oil fruits, nuts or seeds into different sorting passages 8 for good products 2a and 9 for rancid products 2b, depending on the allocated rancidity index value, the sorting passages 8, 9 being implemented by chutes, for example. Based on a predetermined threshold value for the rancidity index value, the computer unit 5 decides to convey the respective oil fruit, the nut or, respectively, the respective seed 2 into one of the sorting passages. The sorting unit 6 can be designed as a flap device, a compressed air device (as shown) or the like. Further embodiments of the sorting unit 6 will be apparent to those skilled in the art from this exemplary reference.

In summary, the present invention as defined in the independent claims and in the preferred embodiments is based on the following concepts and advantages:

The detection and sorting of bulk materials by means of photosensors using hyperspectral imaging (HSI) is a widely used method. In doing so, a sample is irradiated with broadband light, and the reflected light is detected and examined spectroscopically by a photosensor, preferably in the near infrared range. Based on the evaluation of spectra (amplitude, frequency), characteristics and, respectively, ingredients are inferred. The identification of those characteristics, ingredients forms the basis for the differentiation between good and bad products in the sorting process. The identification of those characteristics/ingredients is based on a qualitative, relative approach. In a modelling process, the photometrically detected spectral profiles of good products are compared to the bad product. In doing so, regions of the spectrum are looked for in which the difference in characteristics is very large or, respectively, the correlation to a sought-after substance is very high in contrast to other substances. The identified region(s) is/are then selected for the sorting process, and the respective spectra are normalized. That is, the absolute amplitudes of the spectrum are eliminated, and only the differences between the spectra of the good and bad products are used for the decision in sorting.

Due to this procedure, misclassifications occur for the following reasons:

If the differences between the two spectra are very small, the small difference is enhanced in the normalization process to such an extent that the signal/noise ratio will increase sharply, which greatly increases the uncertainty of the decision.

The differences in the spectrum are determined on the basis of a reference sample of good/bad specimens. However, as far as natural products with spectral scattering are concerned, this comparison is subject to a high level of uncertainty and may vary with each product batch.

The result of this misclassification is an inadequate separation of good and spoiled foods.

This problem arises especially with oil fruits, nuts and seeds when they are processed automatically in production facilities. In this automated processing, the focus is on the desire to automatically distinguish rancid and thus spoiled elements from non-rancid elements. Even before the products are processed further (pressing, grinding, peeling, etc.), individual low-quality fruits/nuts/seeds are to be eliminated in an automated fashion, with a high throughput rate.

The proposed solution is based on a quantitative approach which eliminates the drawbacks of the previous processes in that the sorting information is not gained, as before, from the spectral comparison of rancid oil fruits/nuts/seeds with non-rancid comparative amounts, but the chemical initiators of rancidity (lipid oxidation, hydrolysis) and the substances resulting therefrom (aldehydes, etc.) are examined in terms of their spectral fingerprint.

Since rancidity is not a bivalent quantity, i.e., a mere distinction between rancid/non-rancid is insufficient, but rancidity is present in various degrees, a rancidity index table developed according to the invention is used, which allocates the amplitudes in the respective spectral range to a rancidity value of, e.g., 0-100%.

This rancidity index table is developed on the basis of a statistically large amount of oil fruits/nuts/seeds, using available analytical laboratory methods (e.g., gas chromatography, etc.).

The rancidity index table is now employed according to the invention by using a photosensor of a sorting facility, preferably a hyperspectral camera, for the detection of the degree of rancidity in oil fruits, nuts and seeds, wherein the photosensor can be calibrated with the aid of the rancidity index table of the sorting facility. That is, the quantitative degree (e.g., 0-100%) of rancidity can be inferred automatically from the absolute amplitude in the spectrum in the proper spectral range, based on this table.

The detection process based on the rancidity index table established according to the invention and, respectively, a sorting facility executing this detection process are characterized by the following advantages:

high processing speed and certainty in decision-making in the online sorting process, due to the evaluation of the rancidity index table;

a high-quality rancidity index table, based on the current state of offline laboratory technology, can be used online in the sorting process;

the sorting of rancidity is not a bivalent quantity (rancid/non-rancid), but an analogous quantity which can be traced back on the basis of the amplitude at a certain wavelength or, respectively, on the averages of the amplitudes in a wavelength range;

based on a rancidity value, sorting can be conducted according to different qualities (x % rancidity), and a utilization of different quality levels can thus be achieved;

precise setting of the sorting limit in the sorting facility.

The invention claimed is:

1. A process for establishing a rancidity index table and allocating a rancidity index value to an absorption or reflection spectrum of oil fruits, nuts and seeds, comprising the steps of:
    irradiating a sample of an oil fruit, a nut or a seed with a light source,
    projecting the reflected and/or transmitted light onto a photosensor,
    detecting the absorption or reflection spectrum in a wavelength range from 900 to 2500 nm, by means of the photosensor,
    extracting ingredients of the sample by sample preparation techniques based on a determination of volatile compounds from a vapour space above the sample,
    separating volatile components of the sample by applying gas-chromatographic techniques,
    identifying separated volatile components of the sample by mass spectroscopic detection of constituents of the volatile components which are relevant for lipid oxidation,
    determining a rancidity index value of the sample from identified volatile components of the sample,
    allocating at least individual characteristic wavelengths or wavelength ranges of the detected absorption or reflection spectrum of the sample to the rancidity index value,
    repeating the previous steps for a representative number of samples and forming a rancidity table from the determined rancidity index values and allocated absorption or reflection spectra or, respectively, characteristic wavelengths or wavelength ranges of the detected absorption or reflection spectra.

2. The process according to claim 1, wherein identifying the volatile components of the sample by mass spectroscopic detection of constituents relevant for lipid oxidation comprises identifying one or more groups of substances/functional groups selected from:
    hydroperoxides,
    cyclic hydroperoxides,
    saturated, mono- and di-unsaturated aldehydes,
    hydrocarbons (alkanes, alkenes),
    alcohols (saturated and unsaturated),
    ketones (saturated and unsaturated),
    short chain fatty acids, or
    alkyl furans.

3. The process according to claim 1, wherein the identification of the volatile components of the sample by mass spectroscopic detection of constituents relevant for lipid oxidation occurs by establishing chromatograms at mass/charge ratios selected in a range of between 20 and 300.

4. The process according to claim 3, the process comprising creation of a fatty acid chromatogram at a mass/charge ratio characteristic of fatty acids.

5. The process according to claim 4, process comprising determination of a fatty acid index value by integration across at least a portion of the fatty acid chromatogram.

6. The process according to claim 5, wherein the determination of a rancidity index value occurs by forming the sum of the aldehyde index value and the fatty acid index value.

7. The process according to claim 3, the process comprising creation of an aldehyde chromatogram at a mass/charge ratio characteristic of aldehydes.

8. The process according to claim 7, the process comprising determination of an aldehyde index value by integration across at least a portion of the aldehyde chromatogram.

9. The process according to claim 7, wherein creation of an aldehyde chromatogram at a mass/charge ratio characteristic of aldehydes is at a mass/charge ratio of 44.

10. The process according to claim 3, wherein the identification of the volatile components of the sample by mass spectroscopic detection of constituents relevant for lipid oxidation occurs by establishing chromatograms at one or more mass/charge ratios selected from 43, 44, 55, 56, 57, 60, 70, 71, 73, 74, 81, 83, and 97.

11. The process according to claim 1, wherein the allocation of the detected absorption or reflection spectra of the samples to the rancidity index values is effected by allocating the rancidity index values to at least one of an average, a bandwidth or individual frequency bands of the detected absorption or reflection spectra.

12. The process according to claim 1, wherein the detection of the absorption or reflection spectrum is effected by hyperspectral detection by means of the photosensor.

13. A process for detecting rancidity in an oil fruit, a nut or a seed, comprising the steps of:
    irradiating the oil fruit, nut or seed with at least one light source,
    projecting the reflected and/or transmitted light onto a photosensor,
    detecting an absorption or reflection spectrum in a wavelength range from 900 to 2500 nm, by means of the photosensor,
    providing a rancidity index table according to claim 1 which contains the rancidity index values and the allocated absorption or reflection spectra or, respectively, characteristic wavelengths or wavelength ranges of the absorption or reflection spectrum,
    allocating the detected absorption or reflection spectrum or, respectively, characteristic wavelengths or wavelength ranges of the detected absorption or reflection spectrum to an absorption or reflection spectrum of the rancidity index table which is most similar to the detected absorption or reflection spectrum or, respectively, to characteristic wavelengths or wavelength ranges of the absorption or reflection spectrum,
    determining the rancidity index value allocated to the most similar absorption or reflection spectrum or, respectively, characteristic wavelengths or wavelength ranges of the absorption or reflection spectrum.

14. The process according to claim 13, wherein the allocation of the detected absorption or reflection spectrum to the most similar absorption or reflection spectrum of the rancidity index table is effected by comparing at least one of an average, a bandwidth or individual frequency bands of the absorption or reflection spectra.

15. The process according to claim 13, the process comprising segregation of the oil fruit, nut or seed, if the determined rancidity index value exceeds a threshold value.

16. A device for the detection of rancid oil fruits, nuts or seeds, comprising a light source, a photosensor, a computer unit and a sorting unit, wherein the light source is designed for irradiating the oil fruit, nut or seed, the photosensor is connected to the computer unit and designed for detecting an absorption or reflection spectrum of the light reflected from the oil fruit, nut or seed or transmitted through the oil fruit, nut or seed and transmitting it to the computer unit, and the sorting unit is connected to the computer unit, the computer unit being designed for controlling the sorting unit by executing the process according to claim 13.

17. The process according to claim 13, wherein detecting an absorption or reflection spectrum is in a wavelength range from 900 to 1700 nm, or range from 1000 to 1500 nm.

18. The process according to claim 1, wherein detecting the absorption or reflection spectrum is in a wavelength range from 900 to 1700 nm.

19. The process according to claim 1, wherein detecting the absorption or reflection spectrum is in a wavelength range from 1000 to 1500 nm.

20. The process according to claim 1, wherein extracting ingredients of the sample is by solid phase microextraction.

\* \* \* \* \*